(12) United States Patent
Gammie

(10) Patent No.: US 7,635,386 B1
(45) Date of Patent: Dec. 22, 2009

(54) METHODS AND DEVICES FOR PERFORMING CARDIAC VALVE REPAIR

(75) Inventor: James S. Gammie, Stevenson, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 296 days.

(21) Appl. No.: 11/683,282

(22) Filed: Mar. 7, 2007

Related U.S. Application Data

(60) Provisional application No. 60/780,521, filed on Mar. 7, 2006.

(51) Int. Cl.
*A61F 2/24* (2006.01)
(52) U.S. Cl. ...................................... 623/2.11; 623/904
(58) Field of Classification Search ................. 128/898; 607/9; 623/2.1–2.37, 904
See application file for complete search history.

(56) References Cited

U.S. PATENT DOCUMENTS

| | | | | |
|---|---|---|---|---|
| 6,010,531 | A * | 1/2000 | Donlon et al. | 623/2.1 |
| 6,840,246 | B2 * | 1/2005 | Downing | 128/898 |
| 6,978,176 | B2 * | 12/2005 | Lattouf | 607/9 |
| 7,291,168 | B2 * | 11/2007 | Macoviak et al. | 623/2.36 |
| 7,294,148 | B2 * | 11/2007 | McCarthy | 623/2.36 |
| 2005/0149093 | A1 * | 7/2005 | Pokorney | 606/185 |
| 2006/0100698 | A1 * | 5/2006 | Lattouf | 623/2.11 |
| 2006/0167541 | A1 * | 7/2006 | Lattouf | 623/2.11 |
| 2007/0112422 | A1 * | 5/2007 | Dehdashtian | 623/2.11 |
| 2009/0005863 | A1 * | 1/2009 | Goetz et al. | 623/2.18 |

FOREIGN PATENT DOCUMENTS

WO    WO 2006/078694    7/2006

* cited by examiner

*Primary Examiner*—Suzette J Gherbi
(74) *Attorney, Agent, or Firm*—Squire, Sanders & Dempsey L.L.P.

(57) ABSTRACT

The present invention is directed to methods and devices for repairing a cardiac valve. Generally, the methods involve a minimally invasive procedure that includes creating an access in the apex region of the heart through which one or more instruments may be inserted so as to repair a cardiac valve, for instance, a mitral or tricuspid valve. Accordingly, the methods are useful for performing a variety of procedures to effectuate a repair. For instance, in one embodiment, the methods are useful for repairing a cardiac valve by implanting one or more artificial heart valve chordae tendinae into one or more cardiac valve leaflet tissues so as to restore the proper leaflet function and thereby prevent reperfusion. In another embodiment, the methods are useful for repairing a cardiac valve by resecting a portion of one or more cardiac valve leaflets and implanting one or more sutures into the resected valve tissues, which may also include the implantation of an annuloplasty ring. In an additional embodiment, the methods are useful for performing an edge to edge bow-tie repair (e.g., an Alfieri repair) on cardiac valve tissues. Devices for performing the methods of the invention are also provided.

23 Claims, 9 Drawing Sheets

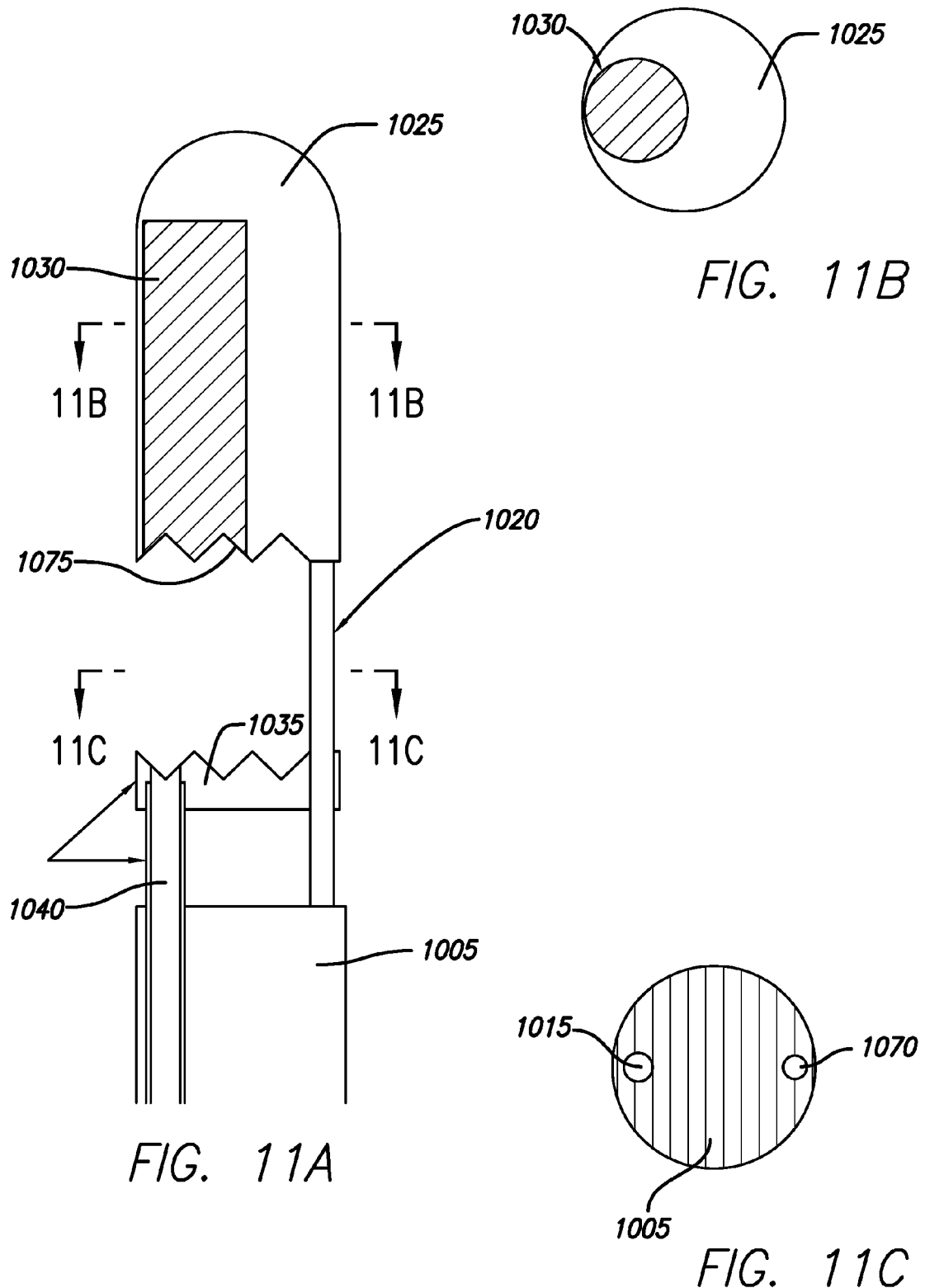

METHODS AND DEVICES FOR PERFORMING CARDIAC VALVE REPAIR

CROSS-REFERENCE TO RELATED APPLICATIONS

This patent application claims the benefit of U.S. Provisional Patent Application No. 60/780,521, filed Mar. 7, 2006, the content of which is incorporated herein by reference in its entirety.

FIELD OF THE INVENTION

The invention relates to methods and devices for performing cardiac valve repairs. Specifically, the invention relates to methods for performing mitral or tricuspid valve repairs.

BACKGROUND OF THE INVENTION

As illustrated in FIG. 1, the human heart (10) has four chambers which include two upper chambers denoted as atria (12, 16) and two lower chambers denoted as ventricles (14, 18). A septum (20) divides the heart and separates the left atrium (12) and left ventricle (14) from the right atrium (16) and right ventricle (18). The heart further contains four valves (22, 24, 26 and 28). The valves function to maintain the pressure and unidirectional flow of the blood through the body and to prevent the blood from leaking back into a chamber from which it has been pumped.

Two valves separate the atria (12, 16) from the ventricles (14, 18), denoted as atrioventricular valves. The left atrioventricular valve, the mitral valve (22), controls the passage of oxygenated blood from the left atrium (12) to the left ventricle (14). A second valve, the aortic valve (24), separates the left ventricle (14) from the aortic artery (aorta) (30), which delivers oxygenated blood via the circulation to the entire body. The aortic and mitral valves are part of the "left" heart, which controls the flow of oxygen-rich blood from the lungs to the body. The right atrioventricular valve, the tricuspid valve (26), controls passage of deoxygenated blood into the right ventricle (18). A fourth valve, the pulmonary valve (28), separates the right ventricle (18) from pulmonary artery (32). The right ventricle (18) pumps deoxygenated blood through the pulmonary artery (32) to the lungs wherein the blood is oxygenated and then delivered to the left atrium (12) via the pulmonary vein. Accordingly, the tricuspid (26) and pulmonic (28) valves are part of the "right" heart, which control the flow of oxygen-depleted blood from the body to the lungs.

Both the left and right ventricles (14 and 18, respectively) constitute "pumping" chambers. The aortic (24) and pulmonic (28) valves lie between a pumping chamber (ventricle) and a major artery and control the flow of blood out of the ventricles and into the circulation. The aortic and pulmonary valves have three cusps, or leaflets, that open and close and thereby function to prevent blood from leaking back into the ventricles after being ejected into the lungs or aorta for circulation.

Both the left and right atria (14 and 16, respectively) are "receiving" chambers. The mitral (22) and tricuspid (26) valves, therefore, lie between a receiving chamber (atrium) and a ventricle so as to control the flow of blood from the atria to the ventricles and prevent blood from leaking back into the atrium during ejection into the ventricle. Both the mitral (22) and tricuspid (26) valves include two or more cusps, or leaflets (not shown), that are encircled by a variably dense fibrous ring of tissues known as the annulus (not shown). The valves are anchored to the walls of the ventricles by chordae tendineae (chordae) (42). The chordae tendineae (42) are cord-like tendons that connect the papillary muscles (44) to the leaflets (not shown) of the mitral (22) and the tricuspid (26) valves of the heart (10). The papillary muscles (44) are located at the base of the chordae (42) and are within the walls of the ventricles. They serve to limit the movements of the mitral (22) and tricuspid (26) valves and prevent them from being reverted. The papillary muscles do not open or close the valves of the heart, which close passively in response to pressure gradients; rather, the papillary muscles brace the valves against the high pressure needed to circulate the blood throughout the body. Together, the papillary muscles (44) and the chordae tendineae (42) are known as the subvalvular apparatus. The function of the subvalvular apparatus is to keep the valves from prolapsing into the atria when they close.

As illustrated with reference to FIG. 2, the mitral valve (100) includes two leaflets, the anterior leaflet (102) and the posterior leaflet (104), and a diaphanous incomplete ring around the valve, the annulus (110). The mitral valve contains two papillary muscles (not shown), the anteromedial and the posterolateral papillary muscles, which attach the leaflets to the walls of the left ventricle via the chordae tendineae (not shown). The tricuspid valve typically is made up of three leaflets and three papillary muscles. However, the number of leaflets can range between two and four. The three leaflets of the tricuspid valve are referred to as the anterior, posterior, and septal leaflets. Although both the aortic and pulmonary valves each have three leaflets (or cusps) they do not have chordae tendineae.

Various disease processes can impair the proper functioning of one or more of the valves of the heart. These disease processes include degenerative processes (e.g., Barlow's Disease, fibroelastic deficiency), inflammatory processes (e.g., Rheumatic Heart Disease) and infectious processes (e.g., endocarditis). Additionally, damage to the ventricle from prior heart attacks (i.e., myocardial infarction secondary to coronary artery disease) or other heart diseases (e.g., cardiomyopathy) can distort the valve's geometry causing it to dysfunction. However, the vast majority of patients undergoing valve surgery, such as mitral valve surgery, suffer from a degenerative disease that causes a malfunction in a leaflet of the valve which results in prolapse and regurgitation.

Generally, there are two different ways that a heart valve may malfunction. One possible malfunction, valve stenosis, occurs when a valve does not open completely and thereby causes an obstruction of blood flow. Typically, stenosis results from buildup of calcified material on the leaflets of the valves causing them to thicken and thereby impairing their ability to fully open and permit adequate forward blood flow.

Another possible malfunction, valve regurgitation occurs when the leaflets of the valve do not close completely thereby causing blood to leak back into the prior chamber. There are three mechanisms by which a valve becomes regurgitant or incompetent; they include Carpentier's type I, type II and type III malfunctions. A Carpentier type I malfunction involves the dilation of the annulus such that normally functioning leaflets are distracted from each other and fail to form a tight seal (i.e., do not coapt properly). Included in a type I mechanism malfunction are perforations of the valve leaflets, as in endocarditis. A Carpentier's type II malfunction involves prolapse of one or both leaflets above the plane of coaptation. This is the most common cause of mitral regurgitation, and is often caused by the stretching or rupturing of chordae tendinae normally connected to the leaflet. A Carpentier's type III malfunction involves restriction of the motion of one or more leaflets such that the leaflets are abnormally constrained below the level of the plane of the annulus. Leaflet restriction can be caused by rheumatic disease (IIIa) or dilation of the ventricle (IIIb).

FIG. 3 illustrates a prolapsed mitral valve (200). As can be seen with reference to FIG. 3, prolapse occurs when a leaflet (202 or 204) of the mitral valve (200) is displaced into the left atrium during systole. Because one or more of the leaflets malfunction the valve does not close properly, and, therefore, the leaflets fail to coapt. This failure to coapt causes a gap between the leaflets (202 and 204) that allows blood to flow back into the left atrium, during systole, while it is being ejected into the left ventricle. As set forth above, there are several different ways a leaflet may malfunction, which can thereby lead to regurgitation.

Although stenosis or regurgitation can affect any valve, stenosis is predominantly found to affect either the aortic and pulmonary valves, whereas regurgitation predominately affects either the mitral or tricuspid valve. Both valve stenosis and valve regurgitation increase the workload on the heart and may lead to very serious conditions if left un-treated; such as endocarditis, congestive heart failure, permanent heart damage, cardiac arrest and ultimately death. Since the left heart is primarily responsible for circulating the flow of blood throughout the body, malfunction of the mitral or aortic valves is particularly problematic and often life threatening. Accordingly, because of the substantially higher pressures on the left side of the heart, left-sided valve dysfunction is much more problematic.

Malfunctioning valves may either be repaired or replaced. Repair typically involves the preservation and correction of the patient's own valve. Replacement typically involves replacing the patient's malfunctioning valve with a biological or mechanical substitute. Typically, the aortic and the pulmonary valves are more prone to stenosis. Because stenotic damage sustained by the leaflets is irreversible, the most conventional treatment for stenotic aortic and pulmonic valves is the removal and replacement of the diseased valve. The mitral and the tricuspid valves, on the other hand, are more prone to deformation. Deformation of the leaflets, as described above, prevents the valves from closing properly and allows for regurgitation or back flow from the ventricle into the atrium, which results in valvular insufficiency. Deformations in the structure or shape of the mitral or tricuspid valve are often repairable.

Valve repair is clearly preferable to valve replacement. Bioprosthetic valves have limited durability. Secondly, prosthetic valves rarely function as well as the patient's own valves. Additionally, there is an increased rate of survival and a decreased mortality rate and incidence of endocarditis for repair procedures. Further, because of the risk of thromboembolism, mechanical valves often require further maintenance, such as the lifelong treatment with blood thinners and anti-coagulants. Therefore, an improper functioning mitral or tricuspid valve is ideally repaired, rather than replaced. However, because of the complex and technical demands of the repair procedures, the overall repair rate in the United States is only around 50%.

Conventional techniques for repairing a cardiac valve are labor-intensive, technically challenging, and require a great deal of hand-to-eye coordination. They are, therefore, very challenging to perform, and require a great deal of experience and extremely good judgment. For instance, the procedures for repairing regurgitating leaflets may require resection of the prolapsed segment and insertion of an annuplasty ring so as to reform the annulus of the valve. Additionally, leaflet sparing procedures for correcting regurgitation are just as labor-intensive and technically challenging, if not requiring an even greater level of hand-to-eye coordination. These procedures involve the implantation of sutures (e.g., ePTFE or GORE-TEX™ sutures) so as to form artificial chordae in the valve. In these procedures, rather than performing a resection of the leaflets and/or implanting an annuplasty ring into the patient's valve, the prolapsed segment of the leaflet is re-suspended using artificial chord sutures. Oftentimes, leaflet resection, annuplasty and neo-cord implantation procedures are performed in conjunction with one another.

Regardless of whether a replacement or repair procedure is being performed, conventional approaches for replacing or repairing cardiac valves are typically invasive open-heart surgical procedures, such as sternotomy or thoracotomy, that require opening up of the thoracic cavity so as to gain access to the heart. Once the chest has been opened, the heart is bypassed and stopped. Cardiopulmonary bypass is typically established by inserting cannulae into the superior and inferior vena cavae (for venous drainage) and the ascending aorta (for arterial perfusion), and connecting the cannulae to a heart-lung machine, which functions to oxygenate the venous blood and pump it into the arterial circulation, thereby bypassing the heart. Once cardiopulmonary bypass has been achieved, cardiac standstill is established by clamping the aorta and delivering a "cardioplegia" solution into the aortic root and then into the coronary circulation, which stops the heart from beating. Once cardiac standstill has been achieved, the surgical procedure may be performed. These procedures, however, adversely affect almost all of the organ systems of the body and may lead to complications, such as strokes, myocardial "stunning" or damage, respiratory failure, kidney failure, bleeding, generalized inflammation, and death. The risk of these complications is directly related to the amount of time the heart is stopped ("cross-clamp time") and the amount of time the subject is on the heart-lung machine ("pump time").

Furthermore, the conventional methods currently being practiced for the implantation of the artificial chordae are particularly problematic. Because the conventional approach requires the heart to be stopped (e.g., via atriotomy) it is difficult to accurately determine, assess and secure the appropriate chordal length. Since the valve will not function properly if the length of the artificial chordae is too long or too short, the very problem sought to be eradicated by the chordal replacement procedure may, in fact, be exacerbated. Using conventional techniques, it is very difficult to ensure that the chordae are of the correct length and are appropriately spaced inside the ventricle to produce a competent valve.

Accordingly, there is a continuing need for new procedures for performing cardiac valve repairs, such as mitral and tricuspid valve repairs, that are less invasive, do not require cardiac arrest, and are less labor-intensive and technically challenging. Chordal replacement procedures that ensure the appropriate chordal length and spacing so as to produce a competent valve are of particular interest. The methods presented herein meet these needs.

SUMMARY OF THE INVENTION

Methods and devices for repairing a cardiac valve are herein provided. Generally, the methods involve a minimally invasive procedure that includes creating an access in the apex region of the heart through which one or more instruments may be inserted so as to repair a cardiac valve, for instance, a mitral or tricuspid valve. Accordingly, the methods are useful for performing a variety of procedures to effectuate a repair. For instance, in one embodiment, the methods are useful for repairing a cardiac valve by implanting one or more artificial heart valve chordae tendineae into one or more cardiac valve leaflet tissues so as to restore the proper leaflet function and thereby prevent valvular regurgitation. In another embodiment, the methods are useful for repairing a cardiac valve by resecting a portion of one or more cardiac valve leaflets and implanting one or more sutures into the resected valve tissues, which may also include the implantation of an annuloplasty ring. In an additional embodiment, the methods are useful for performing an edge-to-edge, bow-tie repair (e.g., an Alfieri repair) on cardiac valve tissues. Devices for performing the methods of the invention are also provided.

Accordingly, in certain embodiments, the methods involve a minimally invasive procedure for repairing a cardiac mitral or tricuspid valve. In certain embodiments, the methods include accessing a mitral valve through the apex region of the left ventricle or accessing a tricuspid valve through the apex region of the right ventricle so as to perform a leaflet repair procedure and/or implant one or more implantable devices into the tissue of the mitral or tricuspid valve or the surrounding tissue. The implantable devices may include sutures, prosthetic or artificial chordae, annuplasty rings or portions thereof, clips, anchors, manifolds, ports, and other such elements configured to support and/or buttress a cardiac repair.

The present invention further includes methods for anchoring the implanted devices, as well as methods for properly knotting (e.g., tying) implanted sutures in such a way that the appropriate length and height of the sutures (e.g., functioning as replacement chordae) can be measured, determined, and adjusted, as necessary, before finishing the procedure. The methods further include evaluating cardiac valve function before tying off and/or cutting implanted sutures.

These and other features, objects and advantages of the invention will become apparent to those persons skilled in the art upon reading the details of the invention as more fully described below.

BRIEF DESCRIPTIONS OF THE DRAWINGS

Figure 10A:
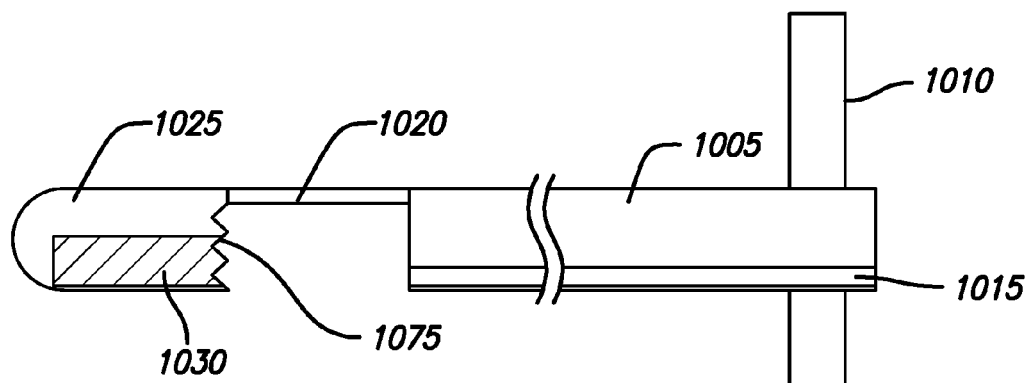
Figure 10B:
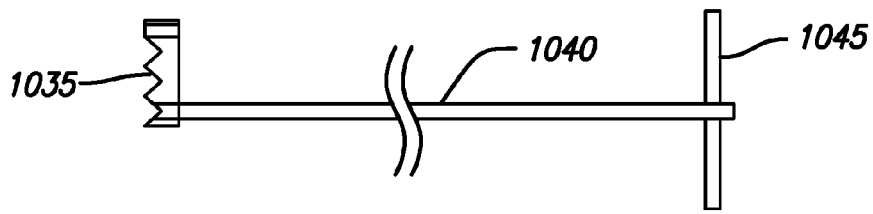
Figure 10C:
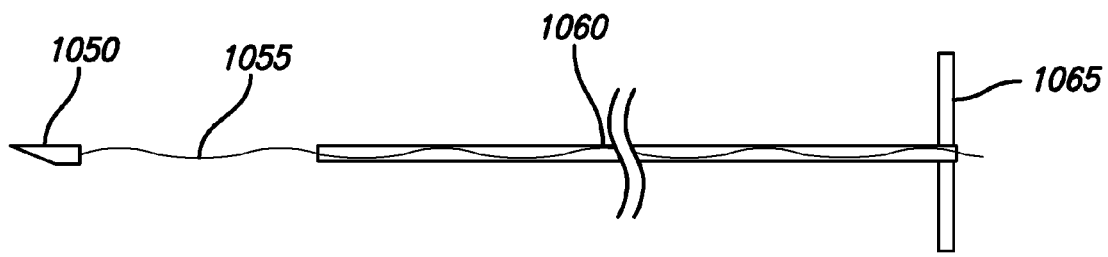

FIGS. 10A-C depict the parts of an example of a device that can be used in the repair methods described herein.

FIG. 11A is a side view of a partially assembled device comprising the parts of FIGS. 10A-C.

FIG. 11B is a cross-sectional view of the cap (1025) and silicone insert (1030) of FIG. 11A.

FIG. 11C is a cross-sectional view of the main body (1005) and its channels (1015 and 1070).

DETAILED DESCRIPTION OF THE INVENTION

The methods disclosed herein set forth minimally invasive procedures that both simplify and expedite cardiac valve repairs. Unlike conventional protocols, the methods herein presented do not involve invasive surgical procedures and do not require cardioplegic arrest and/or lengthy cardiopulmonary bypass. Rather the methods of the invention may be performed while the heart is still beating, thereby reducing if not entirely avoiding pump and cross-clamp time, minimizing pain and trauma, and promoting rapid recovery.

In order to perform a cardiac valve repair of the invention, one or more chambers of the heart must be accessed. Rather than requiring open heart surgery as a means of accessing a chamber of the heart, which necessitates the stopping and bypassing of the heart by an extracorporeal circulation device, the methods of the invention are performed in a minimally invasive manner. Using small incisions, specialized instruments, and/or video/audio-scopic assistance (e.g., endoscopy) the heart may be contacted, the chambers of the heart may thereby be accessed, and a cardiac valve repair procedure performed. These methods may also be performed in a completely percutaneous manner; for instance via the femoral or internal jugular veins, via the inter-atrial septum (trans-septal) and then into the left atrium, or via a retrograde approach (femoral artery, across aortic valve).

Accordingly, the invention is directed to methods for repairing a defective cardiac valve. Specifically, the invention is directed to methods for repairing a cardiac mitral or tricuspid valve so as to reduce or prevent regurgitation. The methods for repairing a defective or malfunctioning mitral or tricuspid valve generally include creating an access in the apex region of the heart through which the defective valve may be accessed and introducing a device through the access so as to repair the cardiac valve by use of the introduced device.

Typically a device for use in accordance with the methods of the invention is configured for implanting one or more other devices (e.g., sutures) into the tissue of the cardiac valve so as to repair the valve and reduce or prevent regurgitation. The tissue within which the one or more devices may be implanted so as to effectuate said repair may be any appropriate tissue such as, but not limited to: an annulus tissue, a leaflet tissue, a chordae tendineae tissue, a papillary muscle tissue, a proximal ventricular tissue, a distal ventricular tissue, an internal or external tissue in the apex region of the ventricle, and/or other suitable myocardial sites, such as the epicardium or pericardium. The methods of the invention will now be described in greater detail herein below.

In accordance with the methods of the invention, the heart may be accessed through one or more openings made by a small incision(s) in a portion of the body proximal to the thoracic cavity, for instance, in between one or more of the ribs of the rib cage, proximate to the xyphoid appendage, or via the abdomen and diaphragm. Access to the thoracic cavity may be sought so as to allow the insertion and use of one or more thorascopic instruments, while access to the abdomen may be sought so as to allow the insertion and use of one or more laparoscopic instruments. Insertion of one or more visualizing instruments may then be followed by transdiaphragmatic access to the heart. Additionally, access to the heart may be gained by direct puncture (i.e., via an appropriately sized needle, for instance an 18 gauge needle) of the heart from the xyphoid region. Access may also be achieved using percutaneous means (see above). Accordingly, the one or more incisions should be made in such a manner as to provide an appropriate surgical field and access site to the heart. See for instance, Full-Spectrum Cardiac Surgery Through a Minimal Incision Mini-Stemotomy (Lower Half) Technique Doty et al. Annals of Thoracic Surgery 1998; 65(2): 573-7 and Transxiphoid Approach Without Median Stemotomy for the Repair of Atrial Septal Defects, Barbero-Marcial et al. Annals of Thoracic Surgery 1998; 65(3): 771-4 which are specifically incorporated in their entirety herein by reference.

After prepping and placing the subject under anesthesia a transesophageal echocardiogram (TEE) (2D or 3D), a transthoracic echocardiogram (TTE), intracardiac echo (ICE), or cardio-optic direct visualization (e.g., via infrared vision from the tip of a 7.5 F catheter) may be performed to assess the heart and its valves. A careful assessment of the location and type of dysfunction on the TEE, TTE, or other such instrument, facilitates the planning of the appropriate surgical procedure to be performed. The use of TEE, TTE, ICE, or the like, can assist in determining if there is a need for adjunctive procedures to be performed on the leaflets and subvalvular apparatus and can indicate whether a minimally invasive approach is advisable.

Once a minimally invasive approach is determined to be advisable, one or more incisions are made proximate to the thoracic cavity so as to provide a surgical field of access. The total number and length of the incisions to be made depend on the number and types of the instruments to be used as well as the procedure(s) to be performed. The incision(s) should be made in such a manner so as to be minimally invasive. By "minimally invasive" is meant in a manner by which an interior organ or tissue may be accessed with as little as possible damage being done to the anatomical structure through which entry is sought. Typically, a minimally invasive procedure is one that involves accessing a body cavity by a small incision made in the skin of the body. By "small incision" is meant that the length of the incision generally should be about 1 cm to about 10 cm, or about 4 cm to about 8 cm, or about 7 cm in length. Additionally, where direct needle access to the heart is sought, the methods of the invention may be performed with even smaller incisions, for instance, an incision of about 1 mm to about 8 mm, from about 3 mm to about 5 mm, or even percutaneously, that is without the need for an incision. The incision may be vertical, horizontal or slightly curved, but if placed along one or more ribs should follow the outline of the rib. The opening should extend deep enough to allow access to the thoracic cavity between the ribs or under the sternum and is preferably set close to the rib cage and/or diaphragm, dependent on the entry point chosen.

One or more other incisions may be made proximate to the thoracic cavity to accommodate insertion of a surgical scope. Such an incision is typically about 1 cm to about 10 cm, or about 3 cm to 7 cm, or about 5 cm in length and should be placed near the pericardium so as to allow ready access to and visualization of the heart. The surgical scope may be any type of endoscope, but is typically a thoracoscope or laparoscope, dependent upon the type of access and scope to be used. The scope generally has a flexible housing and at least a 16× magnification. Insertion of the scope through the incision allows a practitioner to analyze and "inventory" the thoracic cavity and the heart so as to determine further the clinical status of the subject and plan the procedure. For example, a visual inspection of the thoracic cavity may further reveal important functional and physical characteristics of the heart and will indicate the access space (and volume) required at the surgical site and in the surgical field in order to perform the reparative cardiac valve procedure. At this point, the practitioner can confirm that access of one or more cardiac valves through the apex of the heart is appropriate for the particular procedure to be performed.

Suitable devices for use with the methods of the invention are well-known in the art and are commercially available. Typically, the devices are for use in grasping, cutting and/or suturing one or more tissues of the heart from a point of entry into the body that is remote from (e.g., distal to) the heart. Accordingly, a suitable device may be a flexible, elongate member (for instance, a shaft) with a grasping, cutting and/or suturing means attached to the distal end portion of the elongate member. The elongate member may be a cannula, catheter, or the like. A trocar or sheath member may also be used in conjunction with the use of the device so as to facilitate entry and advancement of the device.

The elongate member, for instance, a cannula, is usually of a proportion and circumference to facilitate introduction into the thoracic cavity, through a minimal incision made in the subject's tissue, and of a shape configured to promote advancement of the instrument so as to contact and provide entry into the heart. The diameter of the cannula may be about 0.5 mm to about 10 mm, but is typically about 5 mm. The cannula may include one or a number of shaft members, grasping members, needle members, threading members, de-threading members, and the like that may be moveably coupled to one another. Furthermore, the cannula may be provided with a visual monitoring means such as an endoscope, an ultrasound probe, or the like, so as to check the position of the device in the chest or in the heart. Additionally, the cannula may be provided with suction or vacuum means configured for attaching and positioning a desired tissue relative to the cutting and/or suturing means of the device. Further, the cannula may include an additional shaft configured for delivering a medicament, such as an infusion of heparin, saline for irrigation, or the like to a chamber of the heart where the procedure is being performed.

Additionally, suitable devices for use with the methods of the invention include a handle portion capable of being manipulated so as to finely control the movements of the distal portion members (e.g., the grasping, suturing, and/or cutting means). Exemplary devices that may be adapted for use in accordance with the methods of the invention are set forth in U.S. Pat. Nos. 6,991,635; 6,626,930; 6,921,408; 6,991,635 and U.S. Publication Nos. 2005/0154402, 2003/0094180, 2004/0093023, 2004/0199183, and 2005/0267493, the disclosures of which are hereby incorporated by reference in their entirety. Another example of a device, which can be used to repair a valve, such as a mitral valve, is depicted in FIGS. 10A-C and FIGS. 11A-C. The device comprises a main body (1005), which is from about 9 to about 11 inches in length and comprises a handle (1010) and a channel (1015), and a cap (1025), which comprises a silicone insert (1030) and a jaw (1075). A guide tube (1020), which is connected to the cap (1025), is contained within a channel (1070) in the main body (1005) and adjusts the relative positions of the cap (1025) and the main body (1005). The device further comprises a sliding jaw and tube assembly (FIG. 10B), which comprises a sliding jaw (1035), a handle (1045), and a tube (1040), which slides in the channel (1015) of the main body (1005). The device further comprises a needle and suture push tube assembly (FIG. 10C), which comprises a needle (1050), a suture (1055), and a push tube (1060), which slides in the tube (1040) of the sliding jaw and tube assembly, and a handle (1065). Once the device is inserted through the apex of the heart, such as through a port, an imaging system can be used to position the cap of the device for subsequent clamping of a valve leaflet, such as a mitral valve leaflet. By pushing on the handle (1045) of the sliding jaw and tube assembly (FIG. 10B), the sliding jaw (1035) is closed against the jaw (1075) of the cap (1025), thereby securing the leaflet. With the leaflet secured, the needle and suture push tube assembly is depressed, thereby forcing the needle (1050) through the leaflet and into the silicone insert (1030) of the cap (1025). The push tube assembly is then withdrawn, and the sliding jaw (1075) is returned to its open position. By withdrawing the device from the heart, a loop of suture is formed around the lip of the leaflet and pulled back outside of the heart.

One or more other instruments may additionally be used to facilitate access to the thoracic cavity and/or allow for greater manipulation of the one or more devices used in performing the methods of the invention. For instance, an access platform and/or a vertically or horizontally offsetting retractor may be used to offset one or more ribs of the rib cage and thereby increase access to the thoracic cavity. An organ or tissue positioner may be used to retract or reposition tissues or internal organs at or near the access site or in the thoracic cavity near the site of surgery. A device for stabilizing the beating heart may also be used, if deemed necessary. Devices for beating heart stabilization are described in U.S. Pat. No. 5,727,569 and EPO Application 97/02789.1, which are hereby incorporated in their entirety by reference.

In another embodiment, one or more other instruments may be catheter-based, and access to the left side of the heart (and the mitral valve) may be gained via a percutaneous approach.

Figure 1:
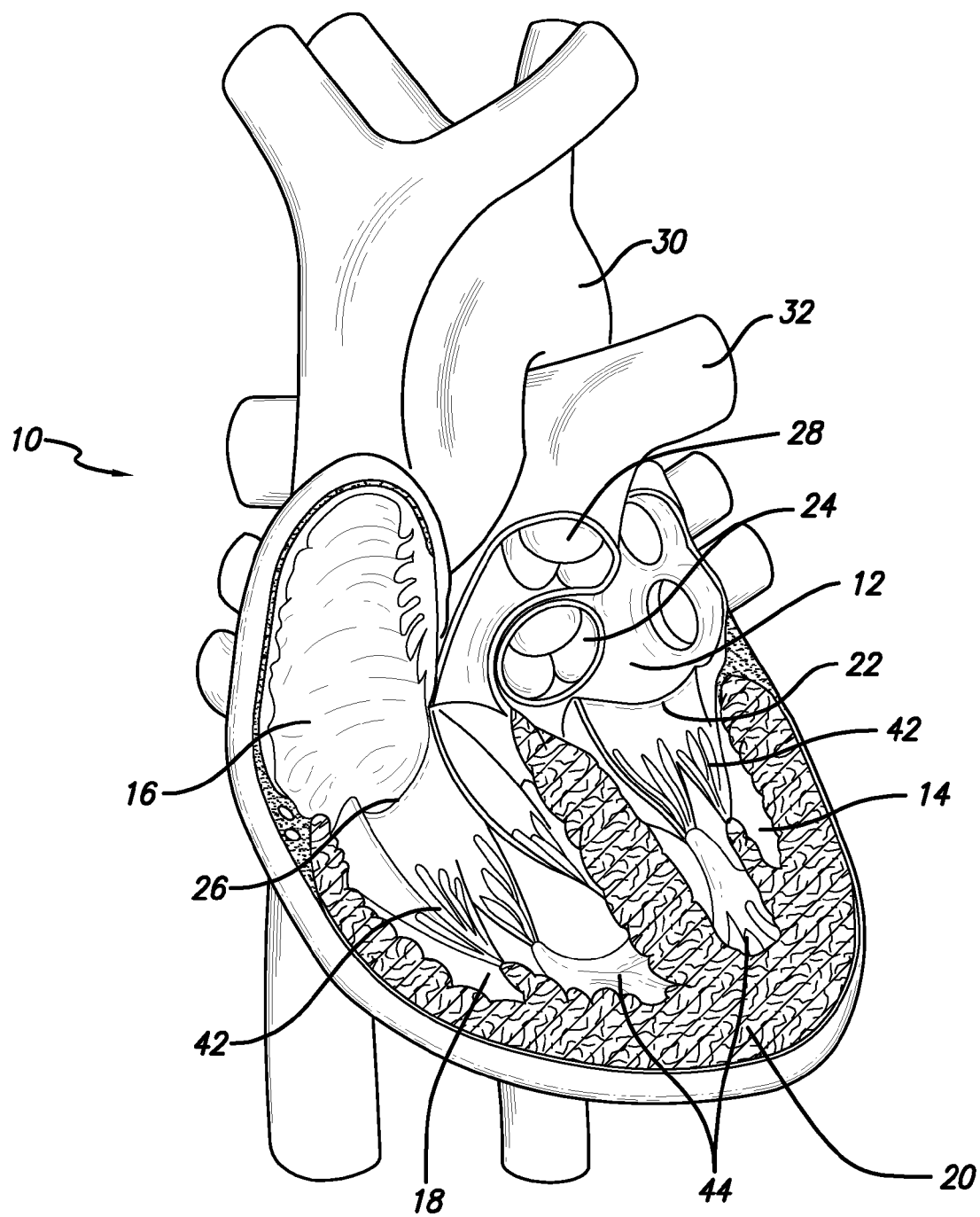
FIG. 1 is a cut-away anterior view of the human heart showing the internal chambers, valves and other adjacent structures.
Figure 2:
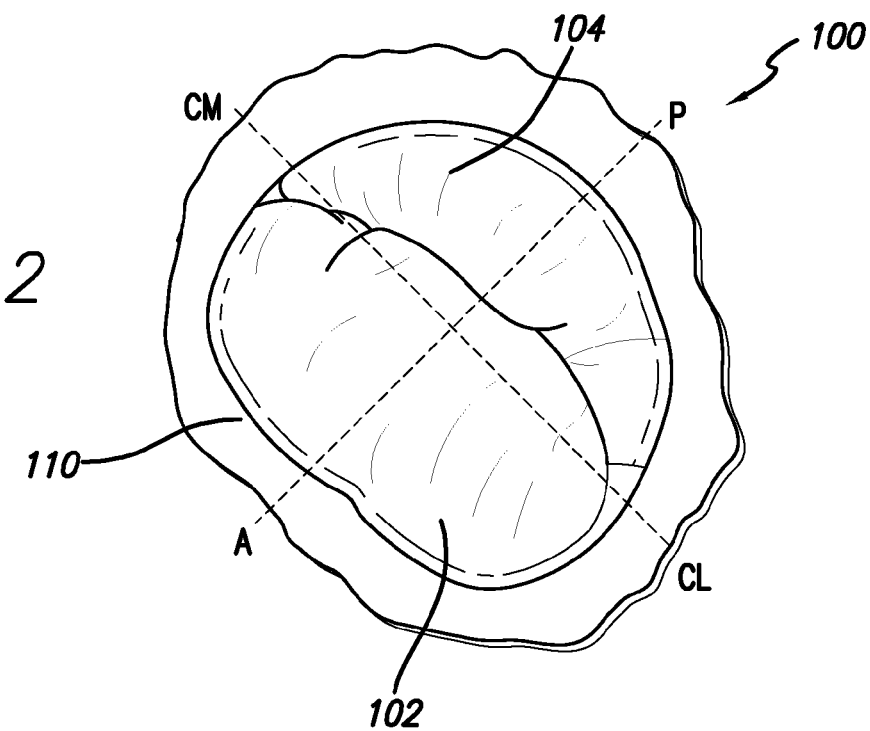
FIG. 2 is a perspective view of a healthy mitral valve with the leaflets closed and coapting at peak contraction pressures during systole.
Figure 3:
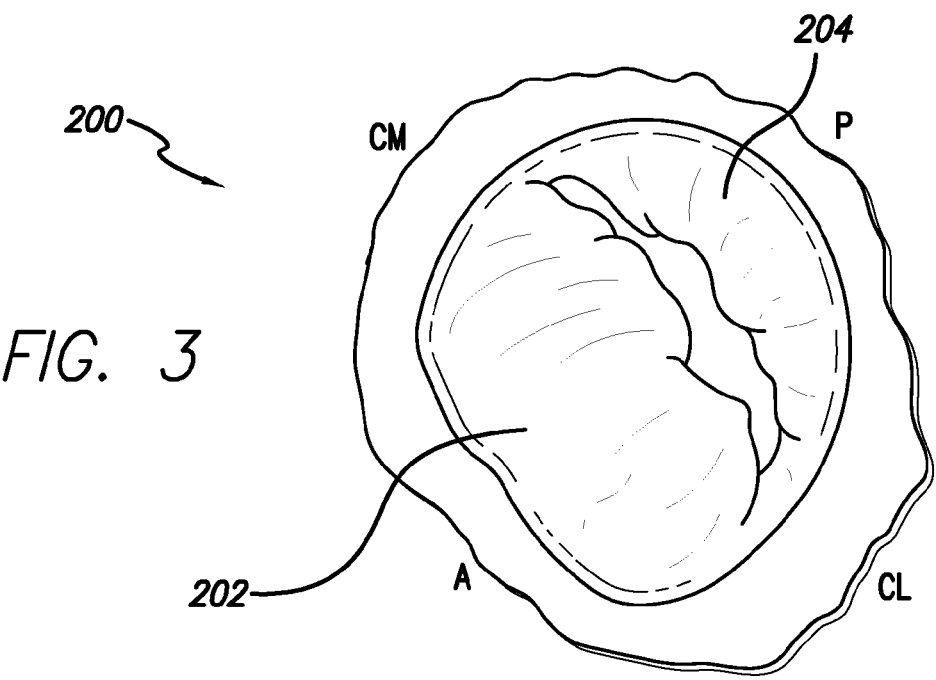
FIG. 3 is a top view of a dysfunctional mitral valve resulting in poor coaptation of the leaflets with a visible gap between them which results in regurgitation of blood into the left atrium during systolic contraction.
Figure 4:
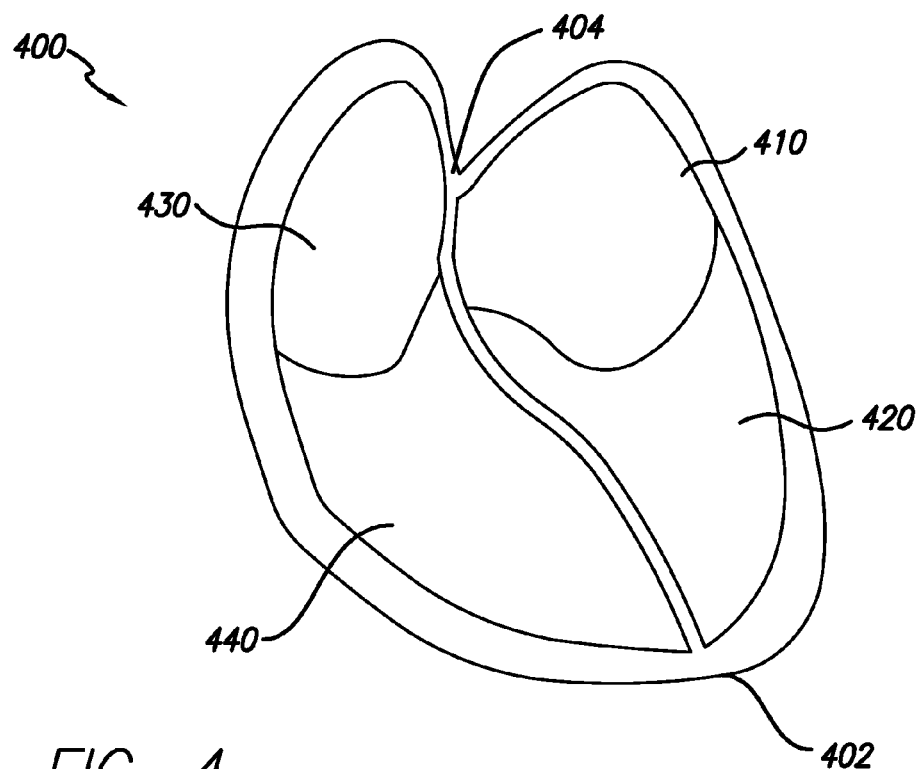
FIG. 4 illustrates an apex region of a heart with four chambers.

With reference to FIG. 4, once a suitable entry point has been established, a suitable device such as one described herein above, may be advanced into the body in a manner so as to make contact with the heart (400). The advancement of the device may be performed in conjunction with sonography or direct visualization (e.g., direct transblood visualization). For instance, the device may be advanced in conjunction with TEE guidance or ICE so as to facilitate and direct the movement and proper positioning of the device for contacting the appropriate apical region of the heart. Typical procedures for use of echo guidance are set forth in Suematsu, Y., J. Thorac. Cardiovasc. Surg. 2005; 130:1348-1356, herein incorporated by reference in its entirety.

One or more chambers (410, 420, 430 or 440) in the heart may be accessed in accordance with the methods disclosed herein. Access into a chamber in the heart may be made at any suitable site of entry but is preferably made in the apex region of the heart (e.g., at the apex) (402). Typically, access into the left ventricle (420), for instance, so as to perform a mitral valve repair, is gained through making a small incision into the apical region, close to (or slightly skewed toward the left of) the median axis (404) of the heart (400). Typically, access into the right ventricle (440), for instance, so as to perform a tricuspid valve repair, is gained through making a small incision into the apical region, close to or slightly skewed toward the right of the median axis (404) of the heart (400). Generally an apex region of the heart is a bottom region of the heart that is within the left or right ventricular region but is distal to the mitral and tricuspid valves and toward the tip or apex (402) of the heart. More specifically, an "apex region" of the heart is within about 20 cm to the right or to the left of the median axis (404) of the heart (400). Accordingly, the ventricle can be accessed directly via the apex, or via an off apex location that is in the apical region but slightly removed from the apex, such as via a lateral ventricular wall, a region between the apex and the base of a papillary muscle, or even directly at the base of a papillary muscle. Typically, the incision made to access the appropriate ventricle of heart is no longer than about 1 mm to about 5 cm, from 2.5 mm to about 2.5 cm, from about 5 mm to about 1 cm in length. When a percutaneous approach is sought, no incision into the apex region of the heart need be made, rather access into the apical region may be gained by direct needle puncture, for instance by an 18 gauge needle, through which an appropriate repair instrument is advanced.

Figure 5:
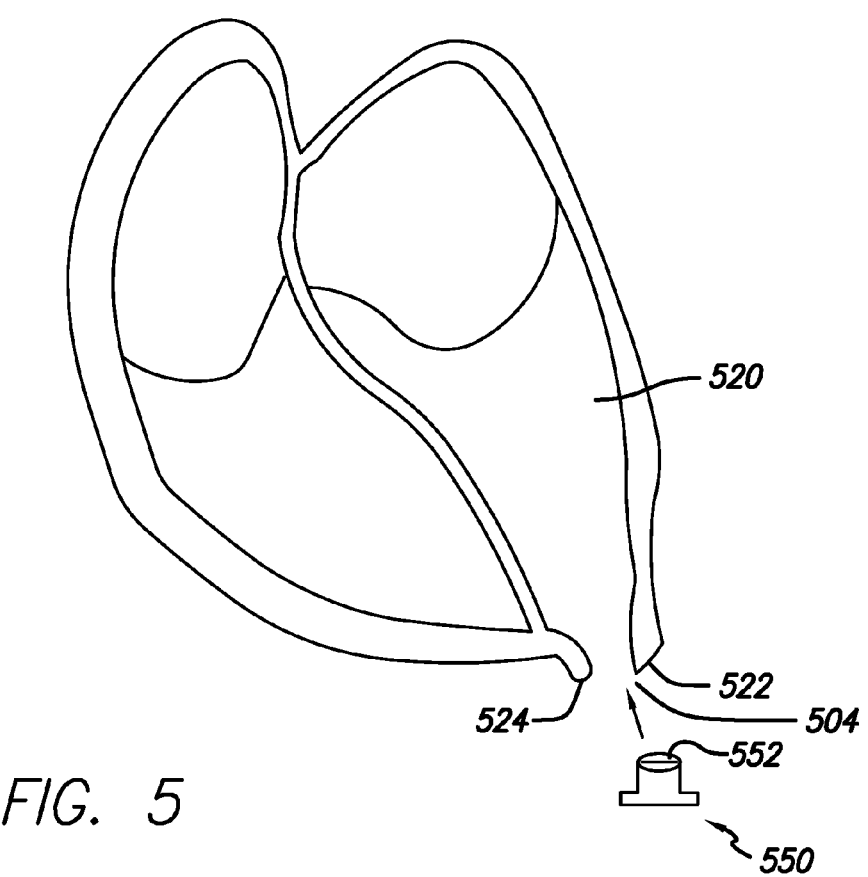
FIG. 5 illustrates an access created in the apex region of the heart.

With reference to FIG. 5, once an incision into the apical region of the appropriate ventricle (e.g., 520) of the heart has been made, the ventricular tissue (522 and 524) may be retracted, if necessary, using a suitable retraction device so as to allow greater access to the cardiac valve in need of repair. For instance, an access port (550) containing a manifold (552) to prevent blood loss as well as air entry into the ventricle, may be inserted into the site of entry (504). Once the chamber is accessed one or more devices (not shown) may be advanced through the access port (550). In some embodiments, a sheath may be inserted through which one or more other instruments are advanced. For instance, an endoscope may first be advanced into the chamber to visualize the ventricle, the valve, and the components thereof. By use of an appropriate endoscope, a careful analysis of the malfunctioning valve may be performed. Each segment of each leaflet may be carefully assessed to determine its pliability, integrity and motion. Based on this assessment, the practitioner can determine whether the valve can indeed be repaired or must be replaced. The motion of the leaflets can be classified as slightly dysfunctional, prolapsed, or restricted and based on this classification the necessary steps of the repair determined.

As explained above both the mitral and tricuspid valves can be divided into three parts—an annulus, leaflets, and a subvalvular apparatus. If the valve is functioning properly, when closed the free margins of the leaflets come together and form a tight junction the arc of which, in the mitral valve, is known as the line of coaptation. The normal mitral and tricuspid valves open when the ventricles relax allowing blood from the left atrium to fill the decompressed ventricle. When the ventricle contracts, the increase in pressure within the ventricle causes the valve to close, thereby preventing blood from leaking into the atrium and assuring that all of the blood leaving the ventricle is ejected through the aortic or pulmonary valves into the arteries of the body. Accordingly, proper function of the valves depends on a complex interplay between the annulus, leaflets and subvalvular apparatus. Lesions in any of these components can cause the valve to dysfunction and thereby lead to valve regurgitation. As set forth above, regurgitation occurs when the leaflets do not coapt at peak contraction pressures. As a result, an undesired back flow of blood from the ventricle into the atrium occurs.

Once the malfunctioning cardiac valve has been assessed and the source of the malfunction verified, a corrective procedure can be performed. Various procedures can be performed in accordance with the methods of the invention to effectuate a cardiac valve repair and will depend on the specific abnormality, the specific component of the valve apparatus affected (e.g., annulus, leaflet segments, cords, papillary muscles, connective tissues, and the like), and the tissues involved.

For instance, if one or more of the chordae tendinae are ruptured, elongated or fused, they can be replaced in accordance with the methods disclosed herein, with one or more artificial cords or by transferring redundant cords from another leaflet section. Shrunken or fused cords can be released or split by precisely cutting the affected cords, and even the papillary muscles, themselves, can be shortened to correct prolapse from multiple elongated cords.

Additionally, in accordance with the methods of the invention, annular calcification can be excised. Excess or prolapsing leaflet tissue can be resected and reconstructed with the implantation of sutures. Leaflet segments can be partially detached from the annulus and advanced to cover a gap from a leaflet resection (known as a sliding valvuloplasty). The circumference and shape of the annulus can be restored with an annuloplasty device (ring or band), which is attached to the annulus using sutures. Alternatively, staples could be deployed in the annulus from the apex of the heart to "cinch down" the diameter of the annulus, or tacks could be placed at various locations in the annulus and pulled together with a suture. Shrunken or restricted leaflet segments can be augmented with a patch of autologous tissue.

Furthermore, where the leaflets of the valves are especially prone to prolapse an edge-to-edge "bow-tie" procedure may be performed so as to implant one or more sutures centrally along the commissure line of two or more leaflets of the cardiac valve to suture the leaflets together and thereby produce a double orifice valve at a central portion of the leaflets. In this regard, a device, which deploys a clip/suture, can be inserted through the apex of the heart and used alone or in combination with a device exemplified herein (see, e.g., figures) to secure a leaflet, suture the leaflet, tie the suture outside of the heart, and cinch it down.

In one embodiment, a method of the invention includes the implantation of one or more artificial chordae tendineae into one or more leaflets of a malfunctioning mitral or tricuspid valve. It is to be noted that, although the following procedures are described with reference to repairing a cardiac mitral or tricuspid valve by the implantation of one or more artificial chordae, the methods herein presented are readily adaptable for various types of leaflet repair procedures well-known and practiced in the art, for instance, an annuloplasty or an Alfieri procedure. Additionally, it is also to be noted that, although the following describes accessing the heart via an apical incision, percutaneous access through direct puncture of the heart (transmyocardial) may also be used, via the insertion of an appropriate grade needle (e.g., an 18 gauge needle) into the apical region of the heart and advancement of a repair instrument, for instance, a catheter, through the lumen of the needle, which is then used to effectuate a repair in accordance with the methods described herein below. Still yet, other percutaneous approaches may be employed where access is made endovascularly through a cut-down or puncture in the femoral or internal jugular veins, and a catheter is delivered therethrough in an antegrade approach through the vena cava into the right atrium and then into the left antrium via the inter-atrial septum (trans-septal). Alternatively, access can be made through the femoral artery and a catheter delivered in a retrograde approach through the aorta, across the aortic valve into the left side of the heart.

Figure 6:
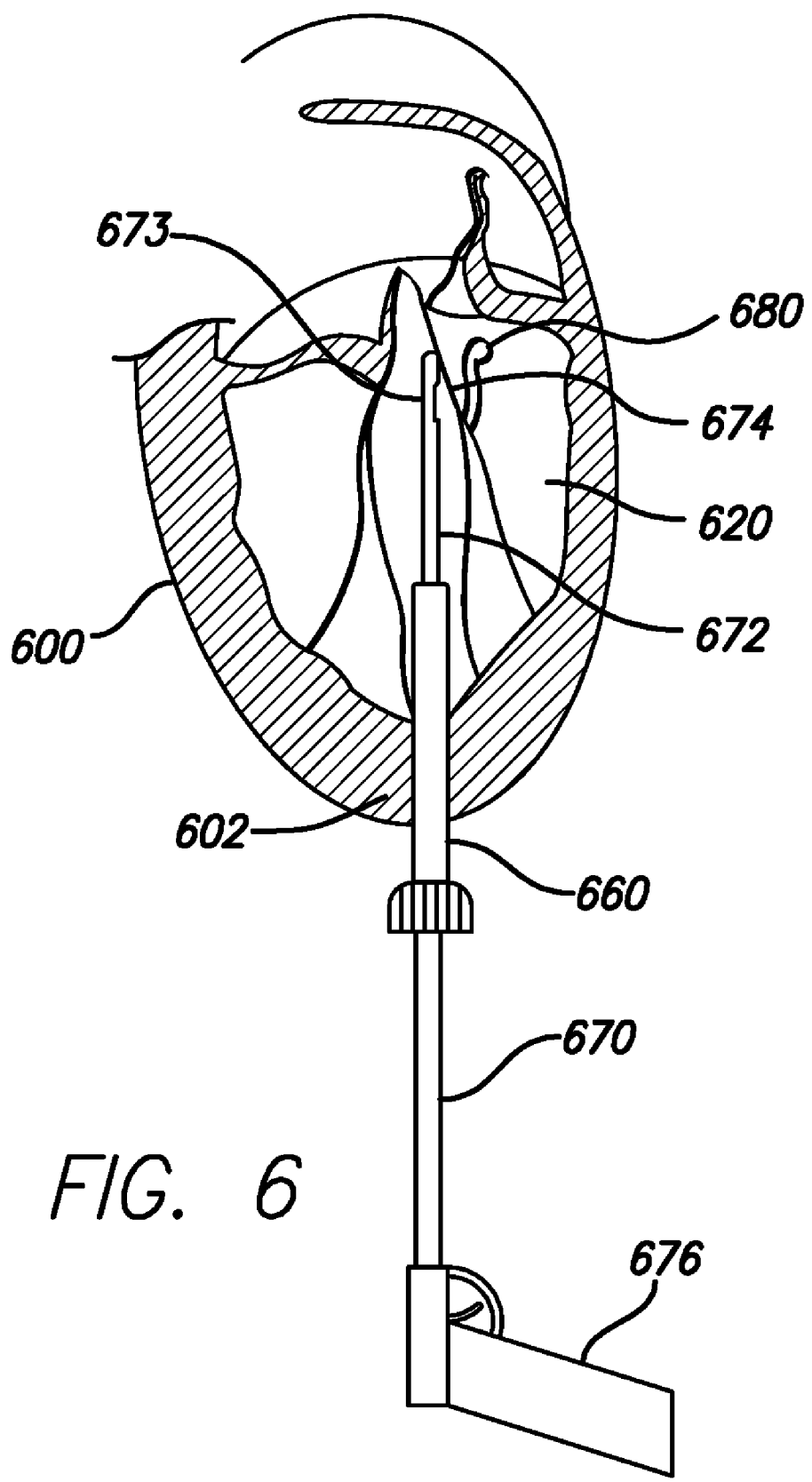
FIG. 6 illustrates the advancement of a device through an accessed region of the heart in accordance with the methods of the invention.

As illustrated in FIG. 6, in accordance with the methods of the invention, once an appropriate incision has been made in the apex region of the heart, for instance, in the apex (602), and a manifold (not shown) and/or sheath (660) inserted, a suitable instrument is then introduced into the ventricle (620) of the heart and advanced in such a manner so as to contact one or more cardiac tissues (for instance, a leaflet, an annulus, a cord, a papillary muscle, or the like) that are in need of repair. Sonic guidance, for instance, TEE guidance or ICE, may be used to assist in the advancement of the device into the ventricle and the grasping of the cardiac tissue with the device. Direct trans-blood visualization may also be used.

Any instrument used in cardiac repair procedures (for instance, chordae replacement procedures) may be used in these procedures with the appropriate modifications. A suitable instrument may be a cannula, catheter, grasping device, suturing device, knotting device, or the like. For example, a suitable instrument (670), such as the one presented in FIG. 6, will typically include an elongate member (672) with a functional distal portion (673) configured for repairing a cardiac valve tissue, for instance, a mitral valve leaflet (680). The functional distal portion (673) of the device is configured for performing one or more selected functions, such as grasping, suctioning, irrigating, cutting, suturing, or otherwise engaging a cardiac tissue. Using a manipulatable handle portion (676), the device (670) is then manipulated in such a manner so that a selected cardiac tissue (for instance, a papillary muscle, one or more leaflet tissues, chordae tendineae, or the like) is contacted with the functional distal portion (673) of the device (670) and a repair effectuated, for instance, a mitral or tricuspid valve repair. The device may additionally contain suction means that is configured for assisting in the grasping and retaining of the cardiac tissue (674).

Figure 7A:
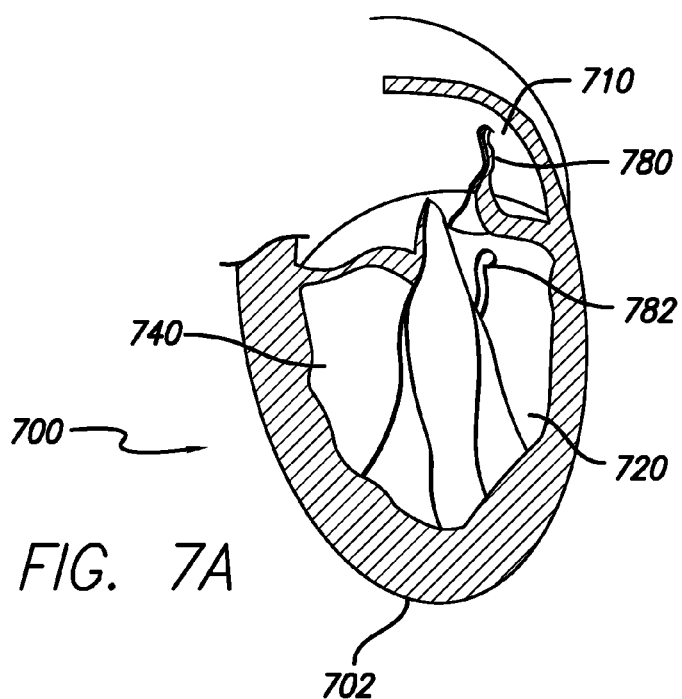
FIG. 7A illustrates a proplapsed mitral valve.

With reference to FIG. 7A, an artificial chordae tendineae implantation procedure for the repair of a malfunctioning mitral valve is illustrated. As can be seen, both the left and right ventricles (720 and 740, respectively) and the apex (702) are shown. A malfunctioning leaflet (780) is shown prolapsed into the left atrium (710). A ruptured chordae tendineae (782) is also shown.

Figure 7B:
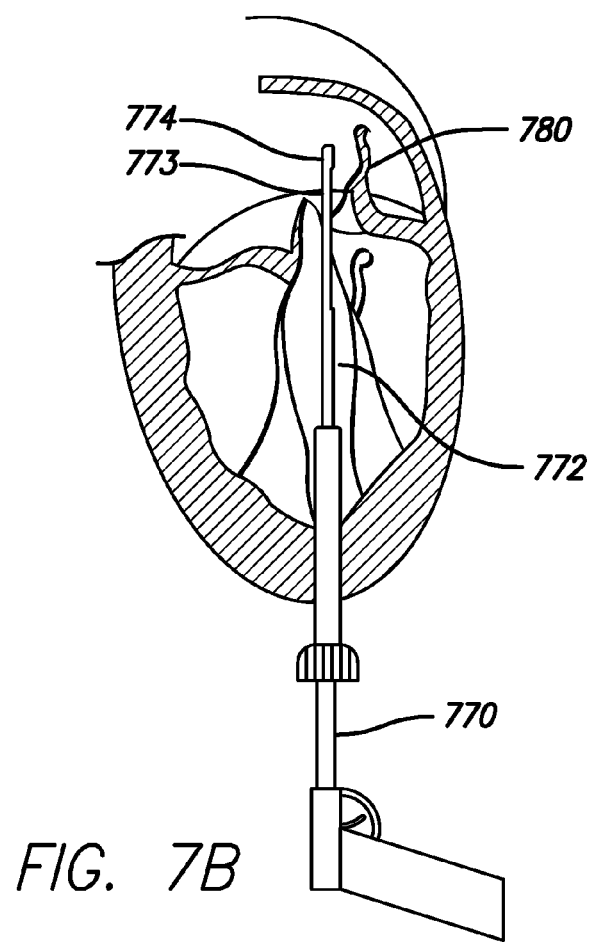
FIG. 7B illustrates an instrument advanced into a left ventricle of the heart so as to repair a prolapsed mitral valve.

As illustrated in FIG. 7B, in accordance with the methods of the invention, the elongate member (772) of the device (770) is advanced so as to contact the leaflet, for instance, the flail segment of the leaflet (780). The device (770) includes a tissue-engaging functional distal portion (773) that is configured for assisting in the repair of the leaflet. The functional distal portion (773) includes a needle-actuating portion (774), which contains a needle actuating member (not shown) configured for actuating a needle in a manner so as to facilitate the implantation of a suture into the leaflet tissue (780). The functional distal portion (773) may also include a suitable grasping means (e.g., a needle, clasp, suction member, or the like) that is configured for assisting in grasping the leaflet tissue (780). Once the needle-actuating portion (774) of the device contacts the leaflet (780) a needle (see FIG. 8, below) is actuated in such a manner as to engage the tissue (780) and a suture is implanted. The leaflet (780) may be engaged in any suitable manner so long as the tissue is grasped and/or the implantation of a suture is implanted by the manipulation of the device.

For instance, in certain embodiments, the edge of the leaflet may be grasped and then displaced apically under echocardiographic vision, to assure that the proper target location on the leaflet has been engaged. Once the proper target location has been engaged, then the needle is deployed, and a suture is implanted. If it is determined that the incorrect target location has been engaged, the leaflet can be disengaged without implanting a suture.

Figure 8B:
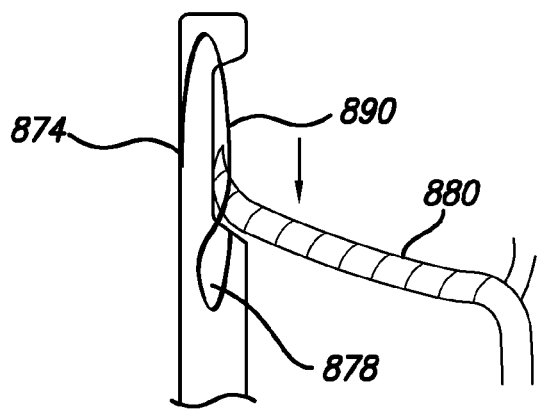
FIGS. 8A-8C illustrate an exemplary repair procedure of the invention.
Figure 8A:
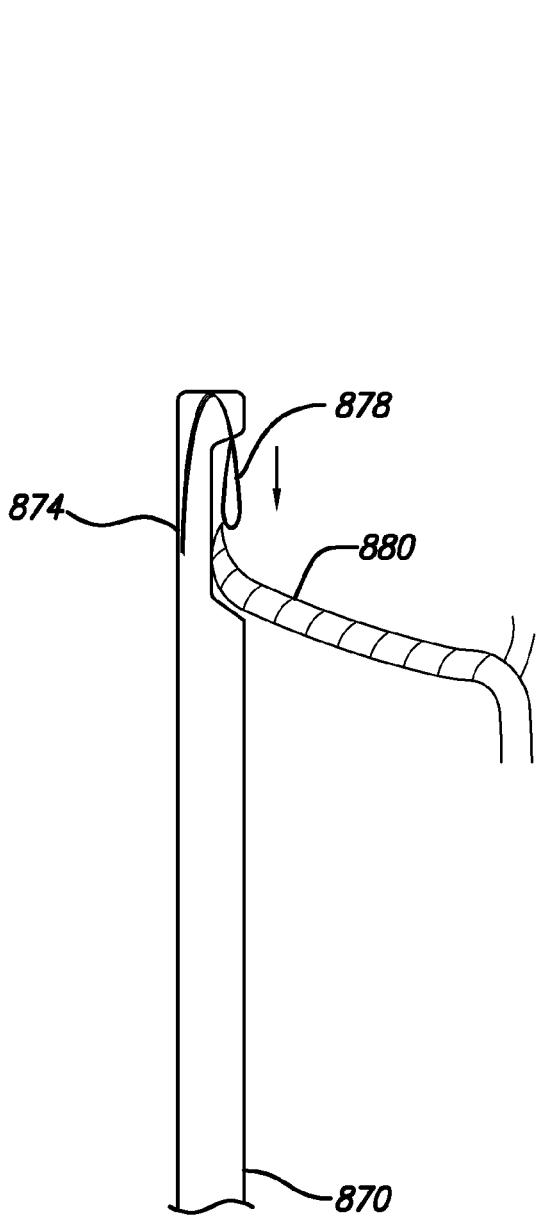
Figure 8C:
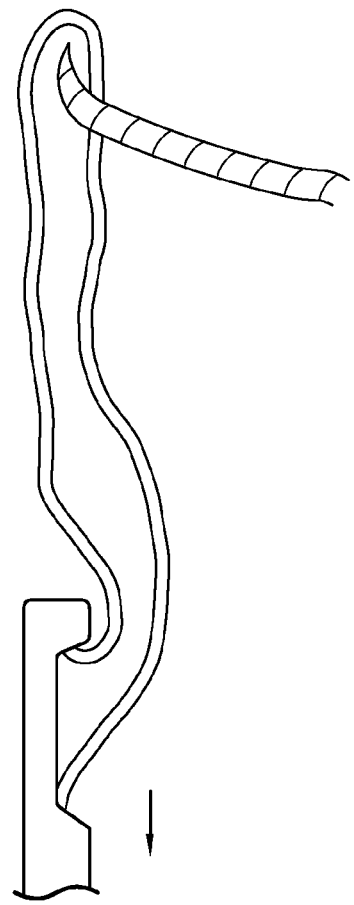

With reference to FIG. 8A, once the flail segment (880) is engaged by the needle-actuating portion (874) of the device (878), a needle (not shown) is actuated and advanced into and through the engaged tissue (as shown in FIG. 8B). The needle may or may not contain a thread upon activation. In one embodiment, the needle is deployable before the suture is passed so as to allow greater control over the implantation of the suture. Accordingly, once the needle (878) is advanced a thread member (not shown)) is actuated so as to attach a thread (890) to the needle (878) and when the needle (878) is withdrawn a suture is deposited through the engaged tissue (as shown in FIG. 8C). Therefore, the needle-actuating member (not shown) actuates a needle (878) and thereby causes one or more sutures (890) to be deposited (e.g., looped) in the engaged tissue (e.g., the flail leaflet tissue). The needle is actuated one or more times, as necessary, with minor adjustments so as to implant or loop one or more sutures in the engaged tissue (e.g., the leaflet tissue).

In one embodiment, once one or more loops of suture(s) are deposited into a first tissue(s), for instance, a leaflet tissue, the ends of the suture(s) may then brought to a position immediately proximal to a second tissue, e.g., a cardiac papillary muscle tissue or other myocardium at the apex region of the heart. The second tissue, e.g., papillary muscle tissue, may then be contacted and engaged by the needle-actuating portion of the device. Once one or more second tissues (e.g., of the papillary muscles) are engaged by the needle-actuating portion of the device, the needle is actuated and advanced into and through the engaged tissue in the manner described above. In accordance with this embodiment, once the needle is advanced a thread member is actuated so as to attach a thread (i.e., a suture) to the needle member and when the needle is withdrawn a suture is deposited through the engaged tissue. Therefore, the needle actuating member actuates a needle and thereby causes a suture to be deposited in (e.g., looped around) the engaged tissue. The needle is actuated one or more times, as necessary, with minor adjustments so as to implant one or more sutures in the engaged tissue (e.g., the papillary muscle tissue). The deposited sutures, therefore, act as an anchor for the artificial chordae that is in the process of being implanted.

It is to be understood that the order of the steps herein described can be interchanged and certain steps omitted without departing from the nature of the invention. Accordingly, although a tissue of one or more leaflets is described as first being engaged by the needle actuating portion of the device, it may just as readily be one or more of a ruptured tendineae, a papillary muscle, a papillary connective tissue, other associated cardiac or ventricular tissue, or the like that is first contacted with the device. Additionally, although only one tissue is hereby described as being engaged it is readily understood that two or more tissues could be engaged with the proper adjustments made. It is also to be understood that these steps can be repeated in any order one or more times so as to implant any necessary number of sutures into the cardiac tissues of the heart. Once fully implanted, the suture(s) acts as a neo-cord, replacing damaged and ruptured chordae tendinae and restoring proper leaflet function. One or more pledgets may also be deposited in conjunction with the sutures for added security.

It is to be noted, that in certain embodiments, the suture to be deposited need not be inserted into an internal anchoring tissue. Rather, the tissue sought to be repaired (e.g., a cardiac valve leaflet) may first be contacted and implanted with one or more sutures and then the sutures may be withdrawn through the apical access and anchored outside of the heart, that is, external to the ventricle chamber. For instance, in certain embodiments, the suture need not first be deposited into an interior anchoring tissue such as the papillary muscle tissue. Rather, one or more sutures need only be implanted into the exact tissue(s) sought to be repaired, for instance, one or more prolapsed leaflets, without first anchoring the sutures to another tissue.

Figure 9:
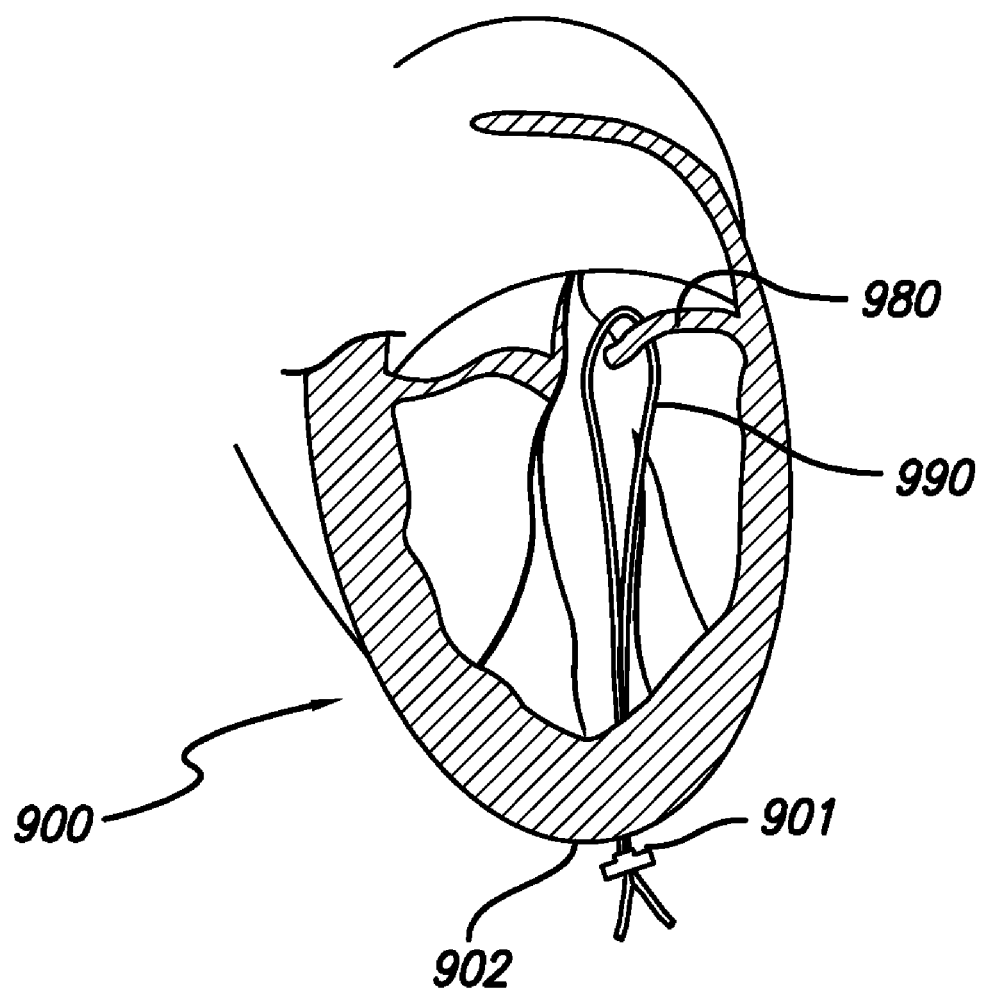
FIG. 9 illustrates a mitral valve repaired in accordance with the methods of the invention.

Accordingly, with reference to FIG. 9, once one or more sutures (990) are deposited into one or more prolapsing leaflets (980) of the malfunctioning cardiac valve, the implantation device (not shown) is withdrawn through the access port (not shown) and the ends of the suture exit the access port therewith out having first been anchored to an interior tissue of the heart. Once outside of the access port, the access port can be removed and the ends of the sutures anchored, in accordance with the methods disclosed below, to a tissue outside of the heart, for instance, epicardial tissue proximal to the apex (902) of the heart (900). One or more purse string sutures may be placed at the entry site along with one or more pledgets (901) so as to securely close the site of entry.

Additionally, in certain embodiments, access to the left side of the heart and the mitral valve is gained via percutaneous techniques. The appropriate instrument on the tip of the catheter is used to deploy a neochord in the free edge of the prolapsing leaflet. Subsequently (or prior to attachment to the leaflet) the other end of the neochord is anchored either in a papillary muscle or in the apical region. Such anchoring may be accomplished by placing a suture in the cardiac muscle, or an anchor of sorts may be deployed in the cardiac muscle (e.g., a T-shaped anchor). Once the neochord is anchored in the myocardium and secured in the free edge of the leaflet, it is shortened to the appropriate length such that mitral regurgitation is minimal or absent.

Variations in the above described procedures may be made without departing from the nature of the invention. For instance, only one suture need be implanted and may first be implanted, for instance, in the papillary muscle and secured thereto with one or more loops or knots. The two ends of the suture may then similarly be implanted through one or more free ends of the valve leaflets, withdrawn through the opening in the apex region of the heart and tied off and/or anchored as described above. Additionally, it may be one or more ruptured or elongated tendinae that are first contacted and implanted with one or more sutures and then one or more leaflets may be implanted with the one or more sutures, or vice versa, and tied off as described above.

Furthermore, in another embodiment, two or more sutures are implanted separately. For instance, in accordance with the methods of the invention, two or more cords can be implanted and tied off to give an appropriate length for the implanted chordae, wherein the two lengths differ from one another. For example, naturally various chordae may have lengths that vary from each other incrementally because of the natural variation that exist between the chordae of the cardiac valve. For instance, within the mitral valve leaflets, the length of the mitral valve chordae increases slightly from the commisures to the center of the leaflet due to the eccentric configuration of the papillary muscles. Accordingly, implanting a number of individual neo-cords having differing chordal lengths may ensure a stronger, tighter closing valve than is currently achievable using the conventional approach.

The sutures that are to be implanted (for instance, so as to function as artificial chordae tenidinae or neo-cords) may be fabricated from any suitable material, such as but not limited here to: polytetrafluoroethylene (PTFE), nylon, Gore-Tex, Silicone, Dacron, or the like. With respect to the implantation of artificial chordae, the particular function of the replacement cord is dependent upon the configuration, physical characteristics and relative positioning of the structure(s). In certain embodiments, the structures act to restrain the abnormal motion of at least a portion of one or more of the valve leaflets. In other embodiments, the prosthetic chordae provide a remodeling as well as a leaflet restraint function where the latter may address latent or residual billowing of the leaflet body and/or latent or residual prolapsing of the leaflet edge, either of which may result from the remodeling itself or from a physiological defect.

It is to be noted that a fundamental challenge in successfully replacing one or more chordae tendineae and restoring proper functioning of a cardiac valve, is determining the appropriate artificial cord length and securing the artificial cord at a location so as to ensure the optimal replacement chordae length. The valve will not function properly if the length of the artificial cord is too long or too short. Because the heart is stopped using conventional techniques, it is virtually impossible to ensure that the cords are of the correct length and are appropriately spaced inside the ventricle to produce a competent valve. Accordingly, methods of the invention include the measuring and determining of the optimal arrangement, length, placement, and configuration of an implanted suture, for instance, a replacement cord length, while the heart is still beating and, typically, before the access site of the heart is closed. An optimal arrangement of a suture, for instance, an optimal cord length, is that arrangement that effectuates said repair, for instance, by minimizing reperfusion as determined by means well known in the art, for instance, by direct echo guidance.

Therefore, in accordance with the methods of the invention, once one or more sutures have been implanted to one or more cardiac tissues, the implantation device is removed through the access (e.g., via the access port), and as stated above, the tail ends of the suture(s) are trailed there through. The optimal length of the implanted suture(s) (i.e., neo-cord) can then be determined by manipulating the ends of the suture (s) in a graded and calibrated fashion that is akin to manipulating a marionette. The manipulation of the sutures may be done in conjunction with audio or visual assistance means, for instance, direct echo (e.g., echocardiographic) guidance, by which the degree and extent of regurgitation can be measured while the chordal length is being manipulated, so as to determine a chordal length that minimizes any observed regurgitation. Since, in a preferred embodiment, the heart is still beating the degree of cardiac regurgitation can be evaluated real time and the optimal neo-cord(s) length determined. Accordingly, an optimal cord length is a cord length that is determined, for instance, by direct echo guidance, to minimize or at least reduce cardiac valve regurgitation. Artificial chordae lengthening or shortening can be performed, as described above, by knotting, tying, cutting, anchoring, and otherwise manipulating the cords in a manner so as to achieve the desired (e.g., optimal) length. Once the optimal length of the neo-cord(s) is determined the sutures can be tied off and/or anchored, outside of the apex, by any means well known in the art, for instance, by tying one or more knots into the suture. One or more pledgets may also be used.

In another embodiment, a method of the invention includes the repairing of a cardiac valve, for instance, mitral or tricuspid valve, by resecting a portion of one or more cardiac valve leaflets and implanting one or more sutures and/or an artificial annuplasty ring into the cardiac valve. In accordance with this embodiment, once an apical access to the heart has been established and an appropriate access port and/or manifold installed, if necessary, the elongate member (e.g., a cannula) of the device may be advanced so as to contact a malfunctioning and disfigured leaflet of a cardiac valve. In this embodiment, the distal end of the elongate member contains a cutting means that is capable of being actuated by an actuation means and may contain an additional grasping means. Accordingly, once the leaflet is contacted with the distal portion of the elongate member of the device, a handle portion is manipulated, and the appropriate leaflet is contacted and/or grasped and resected. Resection of the leaflets may be carried out by techniques well known and practiced in the art. This procedure may be repeated one or more times, at one or more locations, as deemed necessary to properly shape and form the leaflets so as to facilitate proper cardiac valve function. Additionally, the device may further be configured for positioning and implanting one or more annuloplasty devices (e.g., rings) into the tissue of the cardiac valve, in contact with the leaflets.

Accordingly, once the leaflets are resected and/or an annuloplasty ring positioned at a target site, the tissue of the leaflet or annulus may then be contacted with a suturing means such as the one described herein above and one or more sutures may be implanted in the manner set forth above so as to close the resected tissue and/or to implant the annuloplasty ring. The positioning and the configuration of the sutures may be in accordance with any suitable technique including, but not limited to, interrupted mattress sutures, a continuous running suture, interrupted simple (non-mattress) sutures, or the like. One or more specialized clips or staples may also be implanted.

For instance, in one embodiment, an annuloplasty ring is implanted. Once appropriately positioned as desired, a plurality (about 6 to about 15) of horizontal mattress sutures are implanted, with or without the use of pledgets. Additional sutures are then implanted deep into the fibrous substance of the annulus in a tangential direction around its circumference. Complete rings require sutures extending around the complete circumference of the annulus. Partial rings, on the other hand, typically terminate just inside each commissure (a dimple known as the "trigone") and thus do not require placement of sutures along the anterior annulus. The commissural marks on the ring allow the sutures to be properly aligned and the ring to be properly oriented within the annulus. Typically all of the sutures are placed in the annulus and then through the fabric of the annuloplasty ring before being tied and cut. Alternatively the sutures can be placed into the ring after each bite. It is not necessary to suture any of the restraining members, either the primary or secondary restraints, to the valve but this can be done if desired. The sutures can then be tied and cut in accordance with the conventional methods or they may be tied, in a manner as taught herein above with respect to the implantation of the artificial chordae.

Tying the sutures in the manner described above, that is after the optimal functioning of the corrected valve has been determined, is advantageous because the heart is still beating during the implantation procedure and, therefore, before the sutures are finally tied and cut, the repaired valve can be tested to confirm a good line of coaptation without residual regurgitation. Accordingly, once the tissues are resected and/or an annuloplasty device implanted, the device may be withdrawn and the functioning of the valve monitored to ensure proper function. Once optimal valve function is confirmed and the valve repair is complete the sutures can be finally tied and cut, the access port removed, and the apical incision closed. If adjustments need to be made, these can be made before finally tying and cutting the sutures, removing the access port and closing the access opening.

In another embodiment, a method of the invention includes the repairing of a cardiac valve, for instance, a mitral or tricuspid valve, by performing an edge to edge "bow-tie" suturing procedure and thereby effectuating the repair. For instance, such a procedure as set forth in Alfieri O., Maisano, F., et al., "The double-orifice technique in mitral valve repair: a simple solution for complex problems." (2001) Thorac Cardiovasc Surg 122(4):674-681; which is hereby incorporated in its entirety by reference. In accordance with this embodiment, once an apical access to the heart has been established and an appropriate access port and/or manifold installed, the elongate member (e.g., cannula) of the device may be advanced so as to contact a malfunctioning and/or disfigured leaflet of a cardiac valve. In this embodiment the distal end of the elongate member contains a suturing and optionally an additional grasping means, as set forth above.

Accordingly, once one of the leaflets to be sewn together is contacted with the distal portion of the elongate member of the device, the handle portion is manipulated, and the selected leaflet is contacted and/or grasped and a suture is implanted via the advancement and retraction of a needle element as described in greater detail above. The second leaflet is then contacted and the suture is further implanted into the second leaflet. Typically, the suture is implanted centrally along a commissure line along two leaflets so as to suture the leaflets together and thereby produce a double orifice valve at a central portion of the leaflets. This procedure may be repeated one or more times, at one or more locations, as deemed necessary to properly shape and conform the leaflets and to create the double or triple, etc. orifice that prevents prolapse and assists in cardiac valve function. Preferably, the sutures are tied off after the suitable functioning of the bow-tie valve is confirmed in accordance with the methods taught here in. It is noted that although this example is set forth with respect to performing a suturing procedure on the mitral valve it is understood the methods here in are readily adaptable to the other valves of the hear, for instance, the tricuspid valve.

Once the corrective procedures are completed the repaired valve may be further assessed and if the repair is deemed satisfactory, the one or more devices (e.g., cannulae, sheath, manifold, access port, etc.) are removed, the access closed, as described above, and the percutaneous incisions are closed in a fashion consistent with other cardiac surgical procedures. For instance, one or more purse-string sutures may be implanted at the access site of the heart and/or other access sites, so as to close the openings.

Other repair methods, such as the "ring plus string" method (Langer et al., J. Thoracic and Cardiovascular Surgery 133 (1): 247-249 (2007)) and the "papillary muscle sling" method (Hvass et al., Ann. Thorac. Surg. 75: 809-811 (2003)), also can be modified in accordance with the teachings herein. For example, in a modification of the method of Langer et al., a suture is placed via the apex or off-apex, near the base of the papillary muscle, and then the suture is anchored in the base/skeleton of the heart. In a modification of the method of Hvass et al., one can access the heart, such as through a standard 5 mm laparoscopic port, insert a "steerable" guide wire with a very soft tip, guide the wire around the papillary muscles under guidance, grasp the free end of the guide wire with a lasso or closeable loop, and bring the guide wire out through the apex of the heart. A GORETEX™ (or other material) tube/cord then can be attached to the guide wire and brought around the papillary muscles and pulled/tightened as desired to create a complete sling that brings both papillary muscles in close contact. A clip or suture(s) is then used to hold the tube in place. The apex also can be accessed to deploy devices to perform a maze procedure to cure atrial fibrillation. Examples of such devices include a cryoballoon on a catheter, which can be passed across the mitral valve and into the left atrium, where it can cryoablate each of the pulmonary vein ostia. Alternatively, a device can be deployed from the apex to close the left atrial appendage from within the atrium.

While a number of exemplary embodiments have been particularly described, those skilled in the art of cardiac valve repair will appreciate that an unlimited number of device configurations are adaptable for use with the methods provided herein and are, therefore, within the scope of the present invention. The suitability of a particular device configuration, ring configuration, and restraining and/or remodeling structure configuration (if any), and the numerous permutations thereof, will depend on the particularities of the indication(s) being treated and the particular biases of the implanting practitioner. In other words, any suitable neo-chordae, ring shape, contouring, size and thickness may be employed with any suitable restraining and/or remodeling structure configuration (if any) including, any suitable number, spacing, length, thickness, relative positioning and attachment means of the individual restraint or remodeling members being employed.

It is evident from the above description that the features of the subject methods overcome many of the disadvantages of prior art neo-chordae implantation, resection, annuloplasty ring implantation, and valve repair procedures including, but not limited to, minimizing the number or adjunctive procedures and instruments necessary to completely repair a cardiac valve, simplifying the repair procedure allowing more surgeons to offer this procedure to their patients and facilitating minimally invasive approaches to valve repair. As such, the subject invention represents a significant contribution to the field of cardiac valve repair.

It is to be understood that this invention is not limited to particular embodiments described above, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs.

The publications discussed herein are provided solely for their disclosure prior to the filing date of the present application and are incorporated herein by reference to disclose and describe the methods and/or materials in connection with which the publications are cited. Nothing herein is to be construed as an admission that the present invention is not entitled to antedate such publication by virtue of prior invention. Further, the dates of publication provided may be different from the actual publication dates which may need to be independently confirmed.

While the present invention has been described with reference to the specific embodiments thereof, it should be understood by those skilled in the art that various changes may be made and equivalents may be substituted without departing from the true spirit and scope of the invention. In addition, many modifications may be made to adapt to a particular indication, material, and composition of matter, process, process step or steps, while achieving the objectives, spirit and scope of the present invention. All such modifications are intended to be within the scope of the claims appended hereto.

The use of the terms "a," "an," "the," and similar referents in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein, is intended merely to illuminate better the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

REFERENCES

Alfieri O., Maisano, F., et al., "The double-orifice technique in mitral valve repair: a simple solution for complex problems." (2001) *Thorac Cardiovasc Surg* 122(4):674-681.

Braunberger E., Deloche A., et al., "Very long-term results (more than 20 years) of valve repair with Carpentier's techniques in nonheumatic mitral valve insufficiency," (2001) *Circulation* 104 Suppl I:I-8-I-11.

David, T. E., Armstrong, S., et al., "Replacement of chordae tendineae with Gore-Tex sutures: a ten-year experience," (1996) *Heart Valve Dis* 5(4):352-355.

David, T. E., Bos, J., et al., "Mitral valve repair by replacement of chordae tendineae with polytetrafluoroethylene sutures," (1991) *Thorac Cardiovasc Surg* 101(3):495-501.

Duran, C. M. and Pekar, F., "Techniques for ensuring the correct length of new mitral chords," (2003) *Heart Valve Dis* 12(2):156-161.

Eishi, K., Kawazoe, K, et al., "Long-term results of artificial chordae implantation in patients with mitral valve prolapse," (1997) *Heart Valve Dis* 6(6):594-598.

Frater, R. W., "Original chordal sizing article," (1964) *Thorax* 19:458-464.

Frater, R. W., Vetter, H. O., et al., "Chordal replacement in mitral valve repair," (1990) *Circulation* 82(5 Suppl):IV 125-130.

Huber, C. H. and von Segesser, L. K., "Direct Access Valve Replacement (DAVR)—are we entering a new era in cardiac surgery?" (2006) *Eur Cardiothorac Surg* 1-16-06.

Kasegawa, H., Kamata, S., et al., "Simple method for determining proper length of artificial chordae in mitral valve repair," (1994) *Ann Thorac Surg* 57(1):237-238; discussion 238-239.

Kobayashi, J., Sasako, Y., et al., "Ten-year experience of chordal replacement with expanded polytetrafluoroethylene in mitral valve repair," (2000) *Circulation* 102(19 Suppl 3):III 30-34.

Kunzelman, K., Reimink, M. S., et al., "Replacement of mitral valve posterior chordae tendineae with expanded polytetrafluoroethylene suture: a finite element study," (1996) *J Card Surg* 11(2):136-145; discussion 146.

Maisano F., Schreuder, et al., "The double-orifice technique as a standardized approach to treat mitral regurgitation due to severe myxomatous disease: surgical technique," (2000) *Eur Cardiothorac Surg* 17(3):201-205.

Merendino, K. A., Thomas, G. I., et al., "The open correction of rheumatic mitral regurgitation and/or stenosis with special reference to regurgitation treated by posteromedial annuloplasty utilizing a pump-oxygenator," (1959) *Ann Surg* 150(1):5-22.

Minatoya, K., Okabayashi, H., et al., "Pathologic aspects of polytetrafluoroethylene sutures in human heart," (1996) *Ann Thorac Surg* 61(3):883-887.

Mohty D., Orszulak, T. A., et al., "Very long-term survival and durability of mitral valve repair for mitral valve prolapse," (2001) *Circulation* 104 Suppl 1:I-1-I-7.

Nigro, J. J., Schwartz, D. S., et al., "Neochordal repair of the posterior mitral leaflet," (2004) *Thorac Cardiovasc Surg* 127(2):440-447.

Phillips, M. R., Daly, R. C., et al., "Repair of anterior leaflet mitral valve prolapse: chordal replacement versus chordal shortening," (2000) *Ann Thorac Surg* 69(1):25-29.

Sarsam, M. A., "Simplified technique for determining the length of artificial chordae in mitral valve repair," (2002) *Ann Thorac Surg* 73(5):1659-1660.

Savag, E. B., Ferguson, T. B., et al., "Use of mitral valve repair: analysis of contemporary United States experience reported to the society of thoracic surgeons national cardiac database." (2003) *Ann Thorac Surg* 75:820-825.

Suematsu, Y., Martinez, J. F., et al., "Three-dimensional echo-guided beating heart surgery without cardiopulmonary bypass: Atrial septal defect closure in a swine model," (2005) *Thorac Cardiovasc Surg* 130:1348-1357.

Tapia, B. M., Kirsch, M., et al., "Analyse lesionnelle et technique operatoire a propos de 320 cas.," (1998) *Journal de Chirurgie Thoracique et Cardio-Vasculaire* 2:39.

von Oppell, U. O. and Mohr, F. W., "Chordal replacement for both minimally invasive and conventional mitral valve surgery using premeasured Gore-Tex loops," (2000) *Ann Thorac Surg* 70(6):2166-2168.

Zussa, C., "Artificial chordae," (1995) *Heart Valve Dis* 4 Suppl 2: S249-254; discussion S254-256.

Zussa, C., Frater, R. W., et al., "Artificial mitral valve chordae: experimental and clinical experience." (1990) *Ann Thorac Surg* 50(3):367-373.

Zussa, C., Polesel, E., et al., "Seven-year experience with chordal replacement with expanded polytetrafluoroethylene in floppy mitral valve," (1994) *Thorac Cardiovasc Surg* 108(1):37-41.

Zussa, C., Polesel, E., et al., "Surgical technique for artificial mitral chordae implantation," (1991) *Card Surg* 6(4):432-438.

What is claimed is:

1. A method for repairing a defective mitral or tricuspid valve, comprising:
    creating an access in an apical region of a heart through which a defective cardiac valve is accessed;
    introducing a device through said access; and
    repairing said cardiac valve by use of said device,
    wherein the repairing comprises
        replacing one or more chordae tendineae, and
        using said device to implant one or more artificial chordae tendineae, and
    wherein the one or more artificial chordae comprises a suture with one or more leaflets of the heart.

2. The method of claim 1, wherein the repairing comprises resecting one or more leaflets.

3. The method of claim 1, wherein the device is a suturing or stapling device.

4. The method of claim 1, wherein the repairing comprises annuloplasty.

5. The method of claim 1, wherein the repairing comprises stapling or suturing the annulus to create an annuloplasty "effect".

6. The method of claim 1, wherein the repairing comprises performing a bow-tie Alfieri procedure.

7. The method of claim 1, wherein the repair is performed while the heart is beating.

8. The method of claim 1, wherein the method is a minimally invasive procedure.

9. The method of claim 1, wherein the method comprises the use of endoscopy.

10. The method of claim 1, wherein the introduction of the device is performed in conjunction with sonography or direct transblood visualization.

11. The method of claim 1, wherein said repairing comprises:
anchoring the one or more artificial chordae to a tissue in the apical region of the heart.

12. The method of claim 11, wherein the apical tissue is internal to the heart.

13. The method of claim 11, wherein the apical tissue is a papillary muscle, a papillary connective tissue or an endocardial tissue in the lower ventricle.

14. The method of claim 11, wherein the apical tissue is the epicardium.

15. The method of claim 11, further comprising determining an optimal configuration of the one or more artificial chordae before anchoring the artificial chordae.

16. The method of claim 15, wherein the determining comprises the use of sonic guidance.

17. The method of claim 15, wherein the artificial chordae are anchored to the apical tissue subsequent to said determination.

18. The method of claim 1, wherein the repairing comprises the application of a vacuum.

19. A method for treating a defective mitral or tricuspid valve, comprising:
percutaneously accessing an apical region of a heart with a catheter-based device; and
repairing a cardiac valve by use of said device,
wherein the repairing comprises replacing at least one chordae tendineae, and
wherein the replaced chordae tendineae comprises a suture with one or more leaflets of the heart.

20. The method of claim 19, wherein said accessing is done endovascularly via an antegrade approach.

21. The method of claim 19, wherein said accessing is done endovascularly via a retrograde approach.

22. The method of claim 19, wherein said accessing is done via direct access through a transmyocardial approach.

23. The method of claim 19, wherein the replacing comprises anchoring a neochord to the apical region.

* * * * *